(12) United States Patent
Nakamura et al.

(10) Patent No.: US 6,617,139 B1
(45) Date of Patent: Sep. 9, 2003

(54) AMIDASE GENE

(75) Inventors: Tetsuji Nakamura, Kanagawa (JP); Fujio Yu, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/958,969

(22) PCT Filed: Apr. 17, 2000

(86) PCT No.: PCT/JP00/02492

§ 371 (c)(1),
(2), (4) Date: Oct. 16, 2001

(87) PCT Pub. No.: WO00/63354

PCT Pub. Date: Oct. 26, 2000

(30) Foreign Application Priority Data

Apr. 16, 1999 (JP) .......................................... 11-109328

(51) Int. Cl.⁷ ........................... C12P 13/04; C12P 7/56; C12N 9/80; C12N 15/52; C07H 21/04
(52) U.S. Cl. ...................... 435/106; 435/116; 435/136; 435/139; 435/228; 435/252.3; 435/252.33; 435/280; 435/320.1; 536/23.2
(58) Field of Search ................ 435/228, 252.3, 435/252.33, 320.1, 106, 116, 136, 139, 280; 536/23.2

(56) References Cited

U.S. PATENT DOCUMENTS

| 5,215,897 A | 6/1993 | Sakashita et al. ............ 435/106 |
| 5,248,608 A | 9/1993 | Van Dooren et al. ........ 435/280 |
| 5,766,918 A | 6/1998 | Petre et al. .................. 435/228 |
| 5,888,785 A | 3/1999 | Fallon et al. ................ 435/129 |

FOREIGN PATENT DOCUMENTS

| WO | WO 97/12964 | 4/1997 |
| WO | WO 98/01568 | 1/1998 |

OTHER PUBLICATIONS

E. Mahenthiralingam, et al., Journal of General Microbiology, vol. 139, No. 3, pp. 575–583, "Cloning and Sequencing of the Gene Which Encodes the Highly Inducible Acetamidase of Mycobacterium Smegmatis", 1993.

*Primary Examiner*—Elizabeth Slobodyansky
(74) *Attorney, Agent, or Firm*—Oblon, Spivak, McClelland, Maier & Neustadt, P.C.

(57) ABSTRACT

The present invention relates to a novel protein having amidase activity that stereoselectively hydrolyzes α-amino acid amides and α-hydroxy acid amides, and a gene encoding said protein.

30 Claims, 3 Drawing Sheets

SEQUENCE LISTING

<160> NUMBER OF SEQ ID NOS: 2

<210> SEQ ID NO 1
<211> LENGTH: 1444
<212> TYPE: DNA
<213> ORGANISM: Enterobacter cloacae
<220> FEATURE:
<221> NAME/KEY: CDS
<222> LOCATION: (361)..(1305)
<223> OTHER INFORMATION:

<400> SEQUENCE: 1

```
ggatcctcca acttctatgg cccgatcctc ggctgcgcgg gcggtagagg gcggctggaa      60
ctgggcgcgc tactgcaaca aagcgctgga cgcgcaggcg gccgcggcgg acagcatggt     120
gaaacccgac cagcaggacg cgcgcattga agcctggcgc aaaatcttca tcactgcaat     180
ggatgacgcg ccctgggtgc cggtattcaa cgagaagcgc tacaccgtac attccgcacg     240 catgggggc gaggacgctc tgtatgtcga tccagtgcat gtaccagtca actacgacta     300
tatcggactg aaataatttg atggcgccgg gatggcgccg ctgcttaaag gagagtcagg     360 atg tgc caa aat tgt ctg gtg aag acc att cat cat gct caa cat cat       408
Met Cys Gln Asn Cys Leu Val Lys Thr Ile His His Ala Gln His His
 1               5                  10                  15 ttc ggc tgg gat aac agc ctg agc ccg gtc ctg cac gta gct tcc ggc       456
Phe Gly Trp Asp Asn Ser Leu Ser Pro Val Leu His Val Ala Ser Gly
                20                  25                  30 agc caa ctg gag ttt cac tgc ctg gat gcg gct aac ggc tgg ttc aac       504
Ser Gln Leu Glu Phe His Cys Leu Asp Ala Ala Asn Gly Trp Phe Asn
            35                  40                  45 gcc ggt tct acc gca gcg gat atc cca acg ctg ccg ttt gat aag ctc       552
Ala Gly Ser Thr Ala Ala Asp Ile Pro Thr Leu Pro Phe Asp Lys Leu
        50                  55                  60 aac ccg gtc agt ggc ccg gtc tat gtg gaa ggc gct cag ccg ggc gat       600
Asn Pro Val Ser Gly Pro Val Tyr Val Glu Gly Ala Gln Pro Gly Asp
65                  70                  75                  80 gcg cta aag gtg acg ctg gaa tcc ttt cgt ccc agc ggc ttt ggc tgg       648
Ala Leu Lys Val Thr Leu Glu Ser Phe Arg Pro Ser Gly Phe Gly Trp
                85                  90                  95 act gcg aat atc ccg ggc ttc ggc ctg ctg gcc gat cag ttt tct gat       696
Thr Ala Asn Ile Pro Gly Phe Gly Leu Leu Ala Asp Gln Phe Ser Asp
                100                 105                 110
```

```
ccg gcg ctg acg ctg tgg caa tat gac cgc cag ggc tta acc ccc tgc    744
Pro Ala Leu Thr Leu Trp Gln Tyr Asp Arg Gln Gly Leu Thr Pro Cys
            115                 120                 125 gcc ttt ggc cga tat ggc cgc gta ccg ctg aaa ccc ttc gcc ggt acc    792
Ala Phe Gly Arg Tyr Gly Arg Val Pro Leu Lys Pro Phe Ala Gly Thr
        130                 135                 140 ctc ggc gtc gct ccc gcc gcc gcg ggc cat cat tcg gtg gtg ccg ccg    840
Leu Gly Val Ala Pro Ala Ala Ala Gly His His Ser Val Val Pro Pro
145                 150                 155                 160 cgc cgc gtg ggc ggc aat ctg gat att cgc gat ctg gcc gct ggc tgc    888
Arg Arg Val Gly Gly Asn Leu Asp Ile Arg Asp Leu Ala Ala Gly Cys
                165                 170                 175 aca tta tgg cta ccg gtg gaa gta gaa ggc gcg ttg ttt tct att ggt    936
Thr Leu Trp Leu Pro Val Glu Val Glu Gly Ala Leu Phe Ser Ile Gly
            180                 185                 190 gac acc cac gcc gcg cag ggc gat ggt gaa gtc tgc ggc acg gcg att    984
Asp Thr His Ala Ala Gln Gly Asp Gly Glu Val Cys Gly Thr Ala Ile
        195                 200                 205 gaa agc gcg atg gac gtg gtg gtg aag ctg gaa gtg gtt aaa gat atg   1032
Glu Ser Ala Met Asp Val Val Val Lys Leu Glu Val Val Lys Asp Met
    210                 215                 220 ccg ctg aaa acg ccg cgt ttc gcc acc cct ggc cca gtg acc caa cat   1080
Pro Leu Lys Thr Pro Arg Phe Ala Thr Pro Gly Pro Val Thr Gln His
225                 230                 235                 240 ctg gat cgg cac ggc tac agc gcc ttc acc ggc att ggc cct gac ctg   1128
Leu Asp Arg His Gly Tyr Ser Ala Phe Thr Gly Ile Gly Pro Asp Leu
                245                 250                 255 atg acc gcc gcc cgc gac gcg gta agc tat acc atc gat gcg ctg tgc   1176
Met Thr Ala Ala Arg Asp Ala Val Ser Tyr Thr Ile Asp Ala Leu Cys
            260                 265                 270 cgc gaa caa ggg atg tcg gcg gaa gag gcc tat atg ctc tgc tcc gtg   1224
Arg Glu Gln Gly Met Ser Ala Glu Glu Ala Tyr Met Leu Cys Ser Val
        275                 280                 285 tgc ggc gat ctg cgc atc agc gaa atc gtc gat cgg cct aac tgg gtg   1272
Cys Gly Asp Leu Arg Ile Ser Glu Ile Val Asp Arg Pro Asn Trp Val
    290                 295                 300 gtg tcg ttc tat ttt ccc aac agc gtg ttt aat taggagcgtt atgtcagcag  1325
Val Ser Phe Tyr Phe Pro Asn Ser Val Phe Asn
305                 310                 315 tcctatttcc ggcgccgctg ctctcggtcg agcgcctgtc gatccagttt ggtacacagc  1385
gggtggtgga tgacgtcagc tttgcgctct ggccgggaaa aactctgtgc attgccggc   1444

<210> SEQ ID NO 2
<211> LENGTH: 315
<212> TYPE: PRT
<213> ORGANISM: Enterobacter cloacae

<400> SEQUENCE: 2

Met Cys Gln Asn Cys Leu Val Lys Thr Ile His His Ala Gln His His
1               5                   10                  15

Phe Gly Trp Asp Asn Ser Leu Ser Pro Val Leu His Val Ala Ser Gly
            20                  25                  30

Ser Gln Leu Glu Phe His Cys Leu Asp Ala Ala Asn Gly Trp Phe Asn
        35                  40                  45

Ala Gly Ser Thr Ala Ala Asp Ile Pro Thr Leu Pro Phe Asp Lys Leu
    50                  55                  60

Asn Pro Val Ser Gly Pro Val Tyr Val Glu Gly Ala Gln Pro Gly Asp
65                  70                  75                  80
```

-continued

```
Ala Leu Lys Val Thr Leu Glu Ser Phe Arg Pro Ser Gly Phe Gly Trp
             85                  90                  95

Thr Ala Asn Ile Pro Gly Phe Gly Leu Leu Ala Asp Gln Phe Ser Asp
            100                 105                 110

Pro Ala Leu Thr Leu Trp Gln Tyr Asp Arg Gln Gly Leu Thr Pro Cys
            115                 120                 125

Ala Phe Gly Arg Tyr Gly Arg Val Pro Leu Lys Pro Phe Ala Gly Thr
        130                 135                 140

Leu Gly Val Ala Pro Ala Ala Gly His His Ser Val Val Pro Pro
145                 150                 155                 160

Arg Arg Val Gly Gly Asn Leu Asp Ile Arg Asp Leu Ala Ala Gly Cys
                165                 170                 175

Thr Leu Trp Leu Pro Val Glu Val Glu Gly Ala Leu Phe Ser Ile Gly
            180                 185                 190

Asp Thr His Ala Ala Gln Gly Asp Gly Glu Val Cys Gly Thr Ala Ile
            195                 200                 205

Glu Ser Ala Met Asp Val Val Val Lys Leu Glu Val Val Lys Asp Met
    210                 215                 220

Pro Leu Lys Thr Pro Arg Phe Ala Thr Pro Gly Pro Val Thr Gln His
225                 230                 235                 240

Leu Asp Arg His Gly Tyr Ser Ala Phe Thr Gly Ile Gly Pro Asp Leu
            245                 250                 255

Met Thr Ala Ala Arg Asp Ala Val Ser Tyr Thr Ile Asp Ala Leu Cys
            260                 265                 270

Arg Glu Gln Gly Met Ser Ala Glu Ala Tyr Met Leu Cys Ser Val
            275                 280                 285

Cys Gly Asp Leu Arg Ile Ser Glu Ile Val Asp Arg Pro Asn Trp Val
    290                 295                 300

Val Ser Phe Tyr Phe Pro Asn Ser Val Phe Asn
305                 310                 315
```

AMIDASE GENE

CROSS REFERENCE TO RELATED APPLICATION

The present application is a 371 application of PCT/JP00/02492 filed Apr. 17, 2000.

FIELD OF THE INVENTION

The present invention relates to a novel protein having amidase activity that stereoselectively hydrolyzes α-amino acid amides and α-hydroxy acid amides, and a gene encoding said protein.

BACKGROUND OF THE PRESENT INVENTION

It is known that optically active α-amino acids and α-hydroxy acids can be produced using microorganism or enzyme threof as a catalyst to hydrolyze α-amino acid amides and α-hydroxy acid amides. Examples of optically active α-amino acids are described in Japanese Patent Application Laying-Open (kokai) Nos. 61-293394 and 62-55097; optically active α-hydroxy acids are described in Japanese Patent Application Laying-Open (kokai) No. 2-84198.

SUMMARY OF THE INVENTION

Amidase genes cloned via gene recombination techniques can greatly enhance the catalytic capability of microorganisms compared with the conventional methods, because it enables the existence of multiple copies of amidase genes in a cell.

In order to prepare a microbial catalyst having higher catalytic activity, we have completed the present invention by cloning an amidase gene which stereoselectively hydrolyzes α-amino acid amides and α-hydroxy acid amides.

The present invention provides the followings:
(1) A protein defined in the following (a) or (b):
  (a) a protein having an amino acid sequence of SEQ ID NO: 2;
  (b) a protein having an amino acid sequence that differs from the amino acid sequence of SEQ ID NO: 2 by deletion, replacement or addition of one or more amino acids, and having amidase activity that stereoselectively hydrolyzes α-amino acid amides and α-hydroxy acid amides.
(2) A gene which encodes the protein of (1)
(3) The gene of (2) which having a nucleotide sequence of nucleotides 361 to 1305 of SEQ ID NO: 1.
(4) A gene capable of hybridizing to the nucleotide sequence of nucleotides 365 to 1305 of SEQ ID NO: 1 or fragments thereof, and encodes a protein having amidase activity that stereoselectively hydrolyzes α-amino acid amides and α-hydroxy acid amides.
(5) A recombinant vector to which the gene of any one of (2) to (4) is linked.
(6) A transformant which is prepared by introducing the recombinant vector of (5) into a host microorganism.
(7) A method for producing a protein having amidase activity which comprises a culturing process of the transformant of (6)

When a protein having amidase activity, which has been obtained by culturing the above transformant, acts on α-amino acid amides, optically active α-amino acids corresponding thereto can be produced; and when the same protein acts on α-hydroxy acid amides, optically active α-hydroxy acids corresponding thereto can be produced.

This specification includes part or all of the contents disclosed in the specification and/or drawings of Japanese Patent Application No. 11-109328, which is a priority document of the present application.

DETAILED DESCRIPTION OF THE PREFERRED EMBODIMENTS

Figure 1:
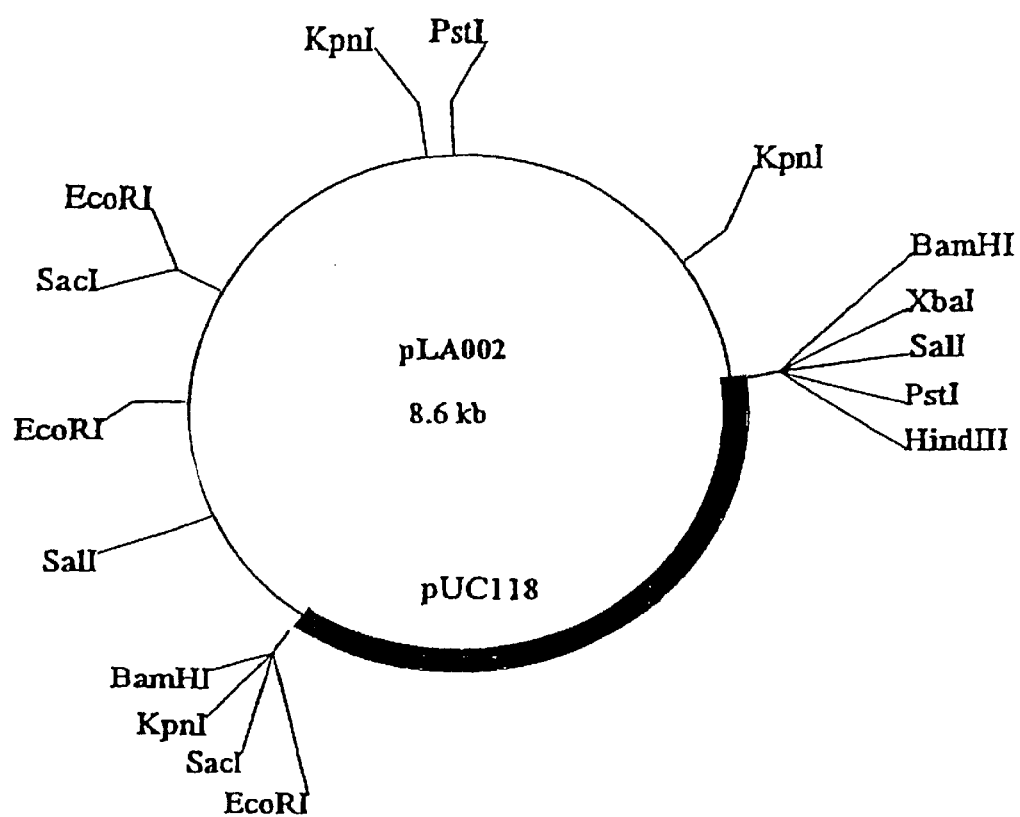
FIG. 1 shows a restriction enzyme map of pLA002.

Now the present invention will be described in detail.

1. Protein and Gene of the Present Invention

The protein of the present invention is a protein having an amino acid sequence of SEQ ID NO: 2 and having amidase activity that stereoselectively hydrolyzes α-amino acid amides and α-hydroxy acid amides. Because of such amidase activity, when the protein of the invention acts on an α-amino acid amide, optically active α-amino acids corresponding thereto can be produced; and when the protein of the invention acts on an α-hydroxy acid amide, optically active α-hydroxy acids corresponding thereto can be produced. Examples of the above α-amino acid amide includes, without limitation, any α-amino acid. A preferred α-amino acid amide is a tert-leucine amide. When the α-amino acid amide is a tert-leucine amide, a D- or L-tert-leucine may be produced as a hydrolytic product, preferably a L-tert-leucine may be produced. Examples of the above α-hydroxy acid amide includes, without limitation, any α-hydroxy acid amide. A preferred α-hydroxy acid amide is a lactic acid amide. When the α-hydroxy acid amide is a lactic acid amide, a D- or L-lactic acid may be produced as a hydrolytic product, preferably a L-lactic acid may be produced. Hence, the above amidase activity is preferably amidase activity that stereoselectively hydrolyzes tert-leucine amides and lactic acid amides, more preferably amidase activity that stereoselectively hydrolyzes tert-leucine amides and lactic acid amides, thereby producing L-tert-leucine and L-lactic acid, respectively.

The amino acid sequence of the protein of the present invention is not limited to the sequence of SEQ ID NO: 2, and may contain a mutation including deletion, replacement or addition of one or more amino acids, as long as the amino acid sequence has the above amidase activity. The number of amino acids to be mutated is not specifically limited, and is preferably 1 to 30, more preferably 1 to several, most preferably 1 to 3 amino acids.

The protein of the present invention as described above may be prepared by known peptide synthesis methods. Further, the protein of the invention can be prepared by gene recombination techniques using DNA encoding the amino acid sequence of the protein of the invention. With the gene recombination techniques, for example the protein of the invention can be prepared by culturing transformants that have been transformed with recombinant plasmids (recombinant vectors) containing the gene of the invention.

The gene of the present invention encodes the above protein of the invention. Thus, the nucleotide sequence of the gene is not limited to a specific sequence, and is preferably a nucleotide sequence encoding an amino acid sequence of SEQ ID NO: 2, more preferably a nucleotide sequence of nucleotides 361 to 1305 of SEQ ID NO: 1. The word "gene" used in the specification means nucleic acids encoding genetic information. The nucleic acids may be DNA or RNA, preferably DNA.

The gene of the present invention can be obtained by a chemical synthesis method, PCR or hybridization using as a probe a gene fragment having the nucleotide sequence. Chemical synthesis, PCR and hybridization can be performed by methods known by persons skilled in the art. In PCR and hybridization, DNA libraries obtained from microorganisms (a microorganism as a DNA donor in the invention) having the gene of the invention can be used. The genera or the species of such microorganisms are not specifically limited. An example of such microorganisms is *Enterobacter cloacae* strain N-7901 (deposited with Accession No. FERM BP-873 on Aug. 16, 1985 to the Patent and Bio-Resource Center, Chuo-6, 1-1-1, Higashi, Tsukuba-shi, Ibaraki, JAPAN) described in the aforementioned Japanese Patent Application Laying-Open (kokai) No. 62-55097. Its bacteriological properties are also described in this application. The said PCR can be performed using the above DNA library as a template and appropriate primers which have been designed based on the nucleotides 361 to 1305 of SEQ ID NO: 1. Other reagents, conditions and the like for the PCR may be appropriately determined by persons skilled in the art, and a commercially available kit can also be used. The hybridization above can be performed by hybridizing a probe having the nucleotide sequence of nucleotides 361 to 1305 of SEQ ID NO: 1 to the DNA library above. Examples of hybridization include methods known by persons skilled in the art, e.g. colony hybridization and plaque hybridization. Conditions for hybridization are not specifically limited, and are preferably stringent conditions. For example, such stringent conditions can be achieved by hybridizing at 42° C. to 68° C. in the presence of 0.5 to 1 M NaCl (or at 42° C. in the presence of 50% formamide or at 65° C. to 68° C. in an aqueous solution) using a filter to which DNA derived from colonies or plaques has been immobilized, and then by washing the filter at room temperature to 68° C. with SSC (saline-sodium citrate) solution at a 0.1 to 2-fold concentration (the composition of SSC solution at 1-fold concentration: 150 mM sodium chloride, 15 mM sodium citrate). Other reagents, conditions and the like for hybridization may be appropriately determined by persons skilled in the art, and a commercially available kit can also be used. Any chemical synthesis method can be employed as long as it is known as a nucleic acid synthesis method. A gene having a desired nucleotide sequence can be obtained by such a chemical synthesis method.

Moreover, a *Escherichia coli* strain JM 109 (*E! coli* JM 109/pLA205) which was transformed with a plasmid pLA205 containing DNA having the nucleotide sequence of nucleotides 361 to 1305 of SEQ ID NO: 1 was deposited on Jan. 26, 1999 to Patent and Bio-Resource Center (Chuo-6, 1-1-1, Higashi, Tsukuba-shi, Ibaraki, Japan) with Accession No. FERM BP-7132. Thus, the gene (DNA) of the present invention having the nucleotide sequence of nucleotides 361 to 1305 of SEQ ID NO: 1 can be obtained from the plasmid pLA205 in the bacterial strain. Other genes of the invention can also be obtained by site-directed mutagenesis (Nucleic Acids Res. 10, 6487-6500, 1982).

Further, the genes of the present invention also include a gene which hybridizes to the nucleotide sequence of nucleotides 361 to 1305 of SEQ ID NO: 1 or fragments thereof, and encodes a protein having amidase activity that stereoselectively hydrolyzes α-amino acid amides and α-hydroxy acid amides. Conditions for hybridization are not specifically limited, and are preferably stringent conditions. For example, such stringent conditions can be achieved by hybridizing at 42° C. to 68° C. in the presence of 0.5 to IM NaCl (or at 42° C. in the presence of 50% formamide or at 65° C. to 68° C. in an aqueous solution), and then by washing the filter at room temperature to 68° C. with SSC (saline-sodium citrate) solution at a 0.1 to 2-fold concentration (the composition of SSC solution at 1-fold concentration: 150 mM sodium chloride, 15 mM sodium citrate).

Furthermore, the genes of the present invention also include a gene, which has at least 90% or more homology, preferably 95% or more homology, more preferably 98% or more homology to the nucleotide sequence of nucleotides 361 to 1305 of SEQ ID NO: 1, and encodes a protein having amidase activity that stereoselectively hydrolyzes α-amino acid amides and α-hydroxy acid amides. The numerical value of homology as described above can be obtained using sequence analysis software, DNASIS (HITACHI Software Engineering), for example by executing maximum matching method command. Parameters are set according to default (initialization settings).

To confirm that a protein having an amino acid sequence other than SEQ ID NO: 2 or a protein encoded by a gene having a nucleotide sequence other than nucleotides 361 to 1305 of SEQ ID NO: 1 has the above amidase activity, *Escherichia coli* strain JM109, which contains a gene encoding a target protein in a condition which allows expression of the gene, is tested for the above amidase activity. Preparation of transformants will be described later. After culturing, the transformed bacterial strains are collected by centrifugation, washed twice with 50 mM $KH_2PO_4$—$Na_2HPO_4$ buffer (pH 8.0) in a volume equal to that of the culture solution, and suspended in 50 ml of the buffer, thereby preparing a cell suspension.

To test for amidase activity described above, a reaction solution consisting of 0.5 ml of the above buffer containing 2 wt % α-amino acid amides or 2 wt % α-hydroxy acid amides, 0.3 ml of the above buffer, and 0.2 ml of the above cell suspension is shaken at 40° C. for 1 hour. The resultant supernatant is analyzed by HPLC provided with an optical resolution column to examine the detection of corresponding, optically active α-amino acids or α-hydroxy acids. Any α-amino acid amide may be used as desired, and preferably a racemic tert-leucine amide may be used. In this case, an optically active α-amino acid to be produced is D- or L-tert-leucine, preferably L-tert leucine. Any α-hydroxy acid amide may be used as desired, and preferably a racemic lactate amide is used. In this case, the optically active α-hydroxy acid to be produced is D- or L-lactic acid, preferably, L-lactic acid.

2. Recombinant Vector and Transformant
(1) Construction of Recombinant Vector

The recombinant vector of the present invention can be constructed by joining (inserting) the gene (DNA) of the invention into an appropriate vector.

Examples of a vector to which the gene of the present invention is inserted, are not specifically limited as long as they can be replicated in a host, and include a plasmid DNA and phage DNA. For example, from microorganisms, e.g. *E. coli* and Agrobacterium, a plasmid DNA can be prepared by the alkaline extraction method (Birnboim, H. C. and Doly, J. 1979. Nucleic Acid Res. 7: 1513) or methods modified therefrom. Examples of a commercially available plasmid vector that may be used herein include pBluescript II SK+(Stratagene), pUC18, pUC19, pUC118, pUC119 (Takara Shuzo Co., Ltd.), and pGEX4T-1 (Pharmacia). Preferably, these plamids contain an ampicillin-resistant gene, kanamycin-resistant gene, chloramphenicol-resistant gene or the like. Examples of a phage vector include λgtll, M13mp18, M13mp19 and the like.

To insert the gene of the present invention into a vector, for example, purified DNA is digested with an appropriate restriction enzyme, and inserted into a restriction enzyme site or a multi-cloning site of an appropriate vector DNA, thereby linking to the vector. Such a procedure is generally performed in the art and can be appropriately performed by persons skilled in the art depending on the specific nucleotide sequence of the DNA to be inserted.

Further, the gene of the present invention should be inserted into a vector such that the gene can perform its function, that is, the gene can be expressed therein. Hence, in addition to a promoter and the gene of the invention, a terminator, ribosome binding sequence and the like may be inserted into the vector of the invention. Such a procedure is generally performed in the art and can be appropriately performed by persons skilled in the art.

(2) Preparation of Transformants

The transformant of the present invention can be obtained by introducing the recombinant vector of the invention into a host so as to allow expression of a target gene.

Examples of a host are not specifically limited as long as they can express the gene of the present invention, and include bacteria and yeast. Examples of bacteria include bacteria belonging to the genus Escherichia, e.g. *E. coli* (*Escherichia coli*) and those belonging to the genus Bacillus, e.g. *Bacillus subtilis*. An example of yeast is *Saccharomyces cerevisiae*. Preferred *Escherichia coli* strains are JM109, C600, IF03301 and the like.

When bacteria, e.g. *E. coli* are used as hosts, a preferred recombinant vector of the present invention can autonomously replicate in the host and comprises a promoter, ribosome binding sequence; the gene of the invention, and a transcription termination sequence. Any promoter can be used as long as it can be expressed in a host e.g. *E. coli*. Examples of promoters that can be used include a Trp promoter, lac promoter, PL promoter, and PR promoter, which are derived from *E. coli* or a phage. The recombinant vector of the invention may also contain a gene that controls a promoter.

Any method for introducing the recombinant vector of the present invention into a bacterium may be employed, and is not specifically limited as long as it allows introduction of DNA into a bacterium. An example of such a method is a method using calcium ions (proc. Natl. Acad. Sci., USA 69: 2110–2114, 1972).

When yeast is used as a host, examples of expression vectors used herein include YEp13, YEp24 and YCp50. Promoters used herein are not specifically limited as long as they can be expressed in a yeast cell. Examples of such a promoter include a gal1 promoter, gal10 promoter, heat shock protein promoter and MFα1 promoter.

Any method for introducing the recombinant vector of the present invention into yeast can be employed, and is not specifically limited as long as it can introduce DNA into yeast. Examples of such a method include electroporation (Methods. Enzymol., 194: 182–187, 1990), spheroplast method (Proc. Natl. Acad. Sci. USA, 84: 1929–1933, 1978), and lithium acetate method (J. bacteriol., 153: 163–168, 1983).

In addition, *Escherichia coli* strain JM 109 (*E. coli* JM r109/pLA205)which was transformed with a plasmid pLA205 containing DNA having the nucleotide sequence of nucleotides 361 to 1305 of SEQ ID NO: 1 was deposited on Jan. 26, 1999 to Patent and Bio-Resource Center (Chuo-6, 1-1-1, Higashi, Tsukuba-shi, Ibaraki, Japan) with Accession No. FERM BP-7132.

3. Production of the Protein (Amidase) of the Present Invention

The protein (amidase) of the present invention can be obtained by culturing transformants prepared as described above, and recovered from the culture product.

Culturing of the transformant of the present invention in a medium is performed by a method generally employed for culturing hosts. A medium for culturing transformants obtained using microorganisms, e.g. *E. coli* or yeast as hosts may be a natural or synthetic medium, as long as it contains carbon, nitrogen and inorganic salt sources, which are assimilable by microorganisms, and allows efficient culturing of transformants.

Examples of carbon sources include carbohydrates, e.g. glucose, fructose, sucrose and starch, organic acids, such as acetic acid and propionic acid and/or alcohol, such as ethanol and propanol.

Examples of nitrogen sources include inorganic acids, e.g. ammonia, ammonium chloride, ammonium sulfate, ammonium acetate and ammonium phosphate, organic acids, e.g. ammonium salt, and other compounds containing nitrogen, e.g. peptone, meat extract and corn steep liquor.

Examples of inorganic salts include potassium primary phosphate, potassium secondary phosphate, magnesium phosphate, magnesium sulfate, sodium chloride, ferrous sulfate, manganese sulfate, copper sulfate and calcium carbonate.

Culturing of transformants obtained using a microorganism as a host is performed under aerobic conditions, such as shake culture and aeration-agitation culture at approximately 28° C. for 48 to 60 hours. During culturing, pH is maintained from 7.0 to 7.5. pH is adjusted with inorganic acid or organic acid, alkaline solution or the like. If necessary, antibiotics, e.g. amplicillin and tetracycline may be added to a medium while culturing.

When microorganisms transformed with an expression vector containing an inducible promoter as a promoter are cultured, an inducer may be added to the medium if necessary. For example, when microorganisms transformed with expression vectors containing Lac promoters are cultured, isopropyl-1-thio-β-D-galactopyranoside (IPTG) or the like may be added to the medium; when microorganisms transformed with expression vectors containing Trp promoters are cultured, indoleacrylic acid or the like may be added to the medium.

After culturing, the protein of the present invention is recovered from the culture product. When the protein is produced within bacteria or within cells, the protein can be recovered by disrupting the bacteria or cells. When the protein is produced outside the bacteria or cells, the culture fluid may be used directly or the bacteria or cells can be removed by e.g. centrifugation, and then the enzyme recovered. The enzyme can be recovered by one of or an appropriate combination of biochemical techniques generally used for isolation and purification of proteins, such as ammonium sulfate precipitation, affinity chromatography, and ion exchange chromatography.

That the protein obtained as described above has the above amidase activity can be confirmed by general enzymologic chemical reaction, electrophoresis, e.g. SDS polyacrylamide gel electrophoresis, immunological techniques, e.g. antigen-antibody reaction, and the like.

Now, cloning of an amidase gene of *Enterobacter cloacae* strain N-7901 into *Escherichia coli* strain JM109 will be described as an example.

EXAMPLE 1

(1) Preparation of *Enterobacter cloacae* N-7901 Chromosomal DNA and Construction of DNA Library The chromosomal DNA of Enterobacter cloacae strain N-7901 was isolated by Saito and Miura's method (see Biochem. Biophys. Acta 72, 619 (1963)). The chromosomal DNA was partially decomposed with a restriction enzyme Sau3AI. Then the gene fragments were sampled by standard techniques and ligated to vector plasmids pUC118, thereby constructing the library of recombinant DNA.

(2) Preparation of Transformants and Selection of Recombinant DNA

Transformants were prepared from the recombinant library prepared in (1) using *Escherichia coli* strain JM109 as a host microorganism by calcium chloride transfection method (J. Mol. Biol., 53,154, (1970)) and then transformants exhibiting amidase activity were selected. Selection was performed as follows.

The transformants were cultured in LB media containing sodium ampicillin (50 µg/ml). After culturing, the culture solution was coated over agar media containing glycerol as a carbon source and leucine amides or lactate amides as a nitrogen source. Colonies formed after culturing at 37° C. for 1 to 3 days were isolated, and then cultured overnight at 37° C. in LB media containing sodium ampicillin (50 µg/ml) and IPTG (1 mM). Next, the cells were collected from the culture solution by centrifugation, and then washed with 50 mM $KH_2PO_4$—$Na_2HPO_4$ buffer (pH 8.0), followed by suspension in the same buffer. The resulting cell suspension was suspended in 50 mM $KH_2PO_4$—$Na_2HPO_4$ buffer (pH 8.0) containing 1% lactate amide, followed by incubation at 30° C. After a certain period of time, the resulting L-lactic acid was quantified by high performance liquid chromatography (column: Sumichiral OA-5000, Sumitomo Chemical Co., Ltd.; eluant: 1 mM copper sulfate aqueous solution; flow rate: 1.0 ml/min; detection: UV 254 nm). Plasmids pLA002 were obtained from transformants that had produced L-lactic acid (FIG. 1).

Figure 2:
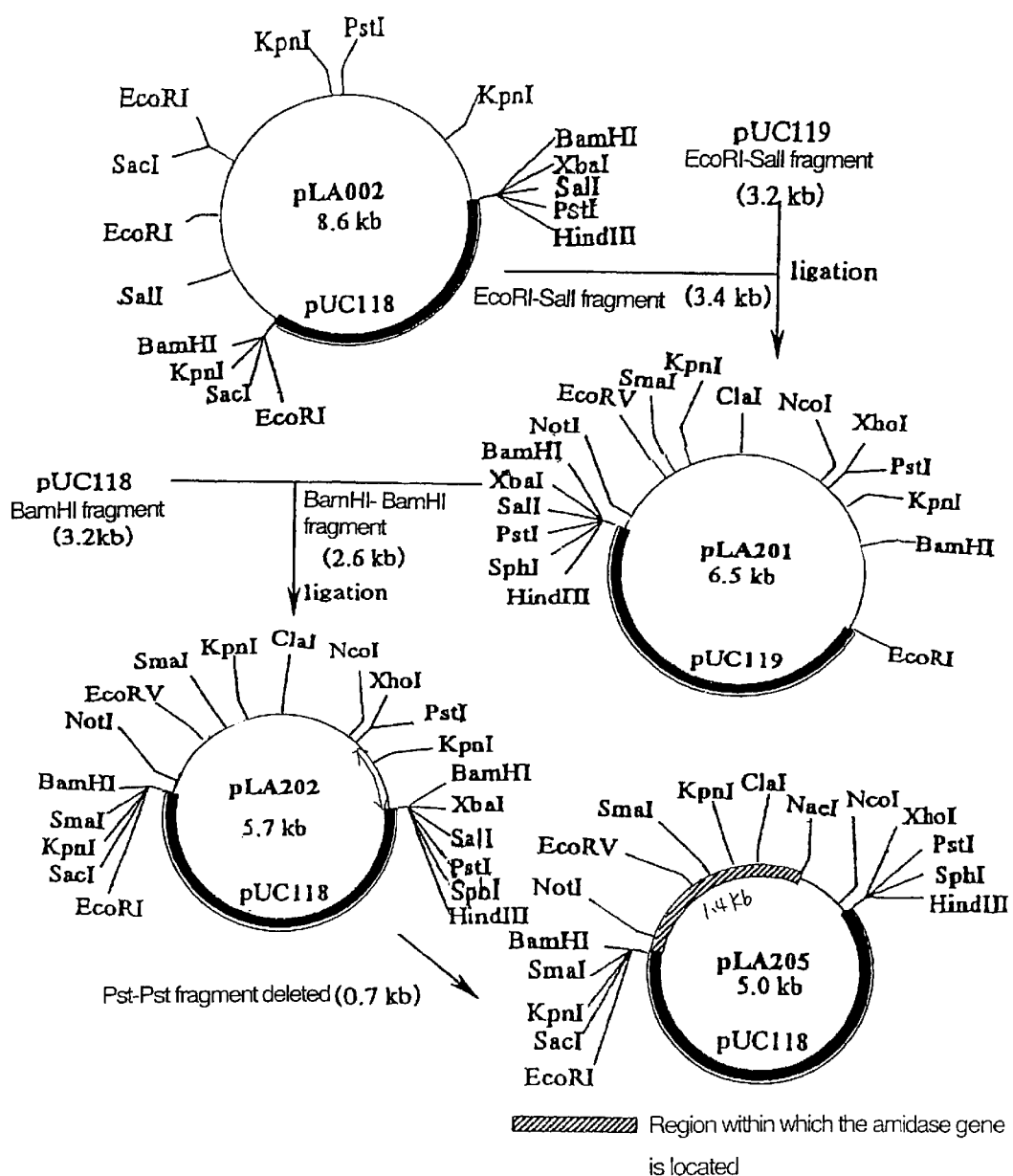
FIG. 2 shows the production process of plasmids from pLA002 to pLA205.

(3) Preparation of Restriction Enzyme Map and Determination of the Position of Amidase Gene A restriction enzyme map was created by standard techniques for the plasmid obtained in (2). Then, a plasmid having smaller DNA fragments was prepared. The strain, which had been transformed with the plasmid in a manner similar to (2), was confirmed to contain a target gene based on the presence of the amidase activity in the strain. FIG. 2 shows the process of plasmid preparation.

That is, an EcoRI-SalI fragment (3.4 kb) of pLA002 was ligated to pUC119, thereby preparing pLA201. Then a BamHI-BamHI fragment (2.6 kb) of pLA201 was ligated to pUC118, preparing pLA202. A PstI-PstI fragment (0.7 kb) of pLA202 was removed from pLA202 so that pLA205 was obtained. Subsequently, various fragments were further removed from pLA205, thereby preparing a plasmid. A portion that may contain a target gene was predicted by examining the presence or absence of the amidase activity in the strain transformed with the plasmid.

(4) Determination of Nucleotide Sequence

Figure 3:
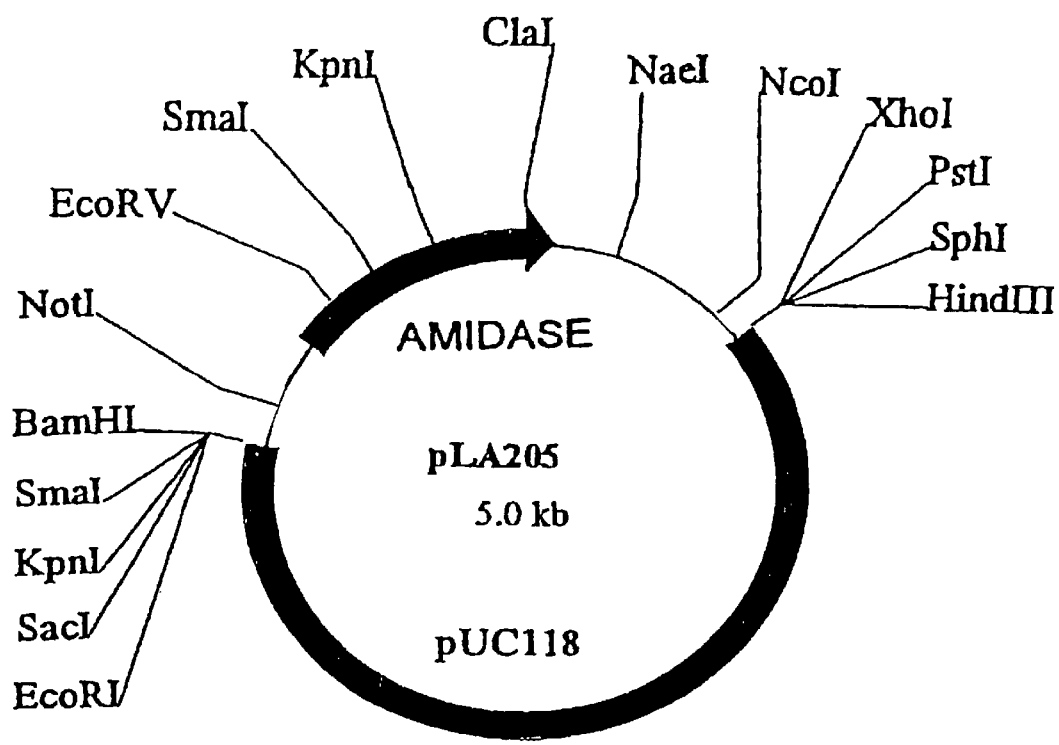
FIG. 3 shows the restriction enzyme map of pLA205.

A nucleotide sequence (DNA) of a BamHI-NaeI portion (1.4 kb) of pLA205 obtained in (3) was determined using a Pharmacia DNA sequencer ALFII. Thus, a nucleotide sequence of SEQ ID NO: 1 was obtained, and an open reading frame (nucleotides 1 361 to 1305 of SEQ ID NO: 1) having the amino acid sequence of SEQ ID NO: 2 was found. FIG. 3 shows the restriction enzyme map of the plasmid pLA205 and the position of amidase.

Comparison with the amino acid sequence database SWISS PROT revealed that the gene of said enzyme has a low homology of 28% to 30% with that of known amidase, e.g. acetoamidase derived from bacteria belonging to the genus Mycobacterium (J. Gen. Microbiol., 139, 575 (1993)) and formamidase derived from bacteria belonging to the genus Methylophilus (Eur. J. Biochem., 240, 314 (1996)) at an amino acid sequence level. This suggests that the enzyme of the gene has totally different enzyme substrate specificity from the known enzymes derived from these bacteria. In addition, the gene has almost no homology with that of known enzymes which stereoselectively hydrolyze amino acid amides. Therefore, the enzyme of the invention is a novel amidase.

*Escherichia coli* strain JM109 (*E. coli* JM109/pLA205) which had been transformed with a plasmid pLA205 containing DNA having the nucleotide sequence of nucleotides 361 to 1305 of SEQ ID NO: 1 was deposited on Jan. 26, 1999 to Patent and Bio-Resource Center (Chuo-6, 1-1-1, Higashi, Tsukuba-shi, Ibaraki, Japan) with Accession No. FERM BP-7132.

EXAMPLE 2

(1) Culturing of *E. coli* strain JM109/pLA205

100 ml of a medium(pH 7.2) consisting of 1% bactotrypton, 0.5% bactoyeast extract, 0.5% NaCl, 0.05% $MgSO_4.7H_2O$, 0.02% $MnSO_4.4$ to $6H_2O$, 0.002% $ZnSO_4.7H_2O$, and 0.002% $CaCl_2.2H_2O$ was put in a 500 ml Erlenmeyer flask, subjected to autoclave sterilization, and then supplemented with sodium ampicillin (50 µg/ml). *E. coli* strain JM109/pLA205 was inoculated to the solution, and then shake-cultured at 37° C. for 19 hours.

(2) Culturing of *Enterobacter cloacae* strain N-7901

The strain was cultured for comparison.

100 ml of a medium (pH 6.0) consisting of 1% sucrose, 0.5% meat extract, 0.5% propione amide, 0.01% $MgSO_4.7H_2O$, 0.001% $MnSo_4.4$ to $6H_2O$, 0.001% $CaCl_2.2H_2O$, 0.001% $FeSO_4.7H_2O$, and 0.0001% $ZnSO_4.7H_2O$ was put in a500 ml Erlenmeyer flask, and then subjected to autoclave sterilization. *Enterobacter cloacae strain N-7901* was inoculated to the solution, and then shake-cultured at 30° C. for 2 days.

(3) Production of Amidase and the Confirmation of the Activity

After culturing, the cells of the each strain were separately collected by centrifugation, washed twice with 50 mM $KH_2PO4$—$Na_2HPO_4$ buffer (pH8.0) in a volume equal to that of the culture solution, and then suspended in 50 ml of the same buffer, thereby preparing a cell suspension. A reaction solution consisting of 0.5 ml of 2% racemic tert-leucine amide, 0.3 ml of 50 $mMKH_2PO_4$—$Na_2HPO_4$ buffer (pH8.0) and 0.2 ml of the cell suspension was shaken at 40° C. for 1 hour. The cells removed by centrifugation from the reaction solution were analyzed by HPLC (column: Sumichiral OA-5000, Sumitomo Chemical Co., Ltd.; eluant: 2 mM copper sulfate aqueous solution/MeOH (85:15); flow rate: 1.0 ml/min; detection: UV254 nm). Enzyme activities of the each bacterial strains were compared (Table 1).

TABLE 1

| Bacterial Strain | Amidase activity (U/mg-dry cell) | Product | Optical Purity of Product (% e.e.) |
|---|---|---|---|
| E. coli JM109/pLA205 | 0.59 | L-tert-leucine | 100 |
| Enterobacter cloacae N-7901 | 0.063 | L-tert-leucine | 100 |

In Table 1, U denotes the production rate (μmol/min) of L-tert-leucine, and amidase activity is shown as a numerical value per dry weight of bacteria contained in the reaction solution.

All the publications, patents and patent applications cited in the present specification are incorporated herein by reference in their entireties.

INDUSTRIAL APPLICABILITY

The present invention allows the multiple presence in a cell of amidase genes cloned via gene recombination techniques. Hence, the present invention can provide a microorganism having a dramatically enhanced catalytic capability compared to the conventional methods, and enables the efficient production of optically active α-amino acids and α-hydroxy acids from α-amino acid amides and α-hydroxy acid amides.

What is claimed is:

1. An isolated protein comprising the amino acid sequence of SEQ ID NO: 2.
2. An isolated polynucleotide which encodes the protein of claim 1.
3. The isolated polynucleotide of claim 2 which comprises nucleotides 361 to 1305 of SEQ ID NO: 1.
4. An isolated polynucleotide, which is capable of hybridizing to the complement of nucleotides 361 to 1305 of SEQ ID NO: 1 under stringent conditions, which comprise washing at 68° C. in 0.1×SSC, and which encodes a protein having amidase activity that stereoselectively hydrolyzes a tert-leucine amide and a lactate amide.
5. A recombinant vector comprising the isolated polynucleotide according to claim 2.
6. A transformed host cell comprising the recombinant vector of claim 5.
7. A method for producing a protein having amidase function, which comprises culturing the transformed host cell of claim 6.
8. A recombinant vector comprising the isolated polynucleotide according to claim 3.
9. A transformed host cell comprising the recombinant vector of claim 8.
10. A method for producing a protein having amidase activity which comprises culturing the transformed host cell of claim 9.
11. A recombinant vector comprising the isolated polynucleotide according to claim 4.
12. A transformed host cell comprising the recombinant vector of claim 11.
13. A method for producing a protein having amidase activity which comprises culturing the transformed host cell of claim 12.
14. An isolated polynucleotide which is at least 90% homologous to nucleotides 361 to 1305 of SEQ ID NO: 1 and which encodes a protein having amidase activity that stereoselectively hydrolyzes a tert-leucine amid and a lactate amide.
15. A recombinant vector comprising the isolated polynucleotide of claim 14.
16. A transformed host cell comprising the recombinant vector of claim 15.
17. A method for producing a protein having amidase activity which comprises culturing the transformed host cell of claim 16.
18. The method of claim 7, which further comprises recovering the protein produced from the cultured transformed host cell.
19. The method of claim 10, which further comprises recovering the protein produced from the cultured transformed host cell.
20. The method of claim 13, which further comprises recovering the protein produced from the cultured transformed host cell.

21. The method of claim 17, which further comprises recovering the protein produced from the cultured transformed host cell.

22. A method of preparing an optically active α-amino acid, α-hydroxy acid or both, comprising contacting a racemic mixture of an α-amino acid amide, an α-hydroxy acid amide or a mixture thereof with the isolated protein of claim 1.

23. A method of preparing an optically active α-amino acid, α-hydroxy acid or both, comprising producing a protein according to claim 7 and contacting a racemic mixture of an α-amino acid amide, an α-hydroxy acid amide or a mixture thereof with the protein produced.

24. A method of preparing an optically active α-amino acid, α-hydroxy acid or both, comprising producing a protein according to claim 10 and contacting a racemic mixture of an α-amino acid amide, an α-hydroxy acid amide or a mixture thereof with the protein produced.

25. A method of preparing an optically active α-amino acid, α-hydroxy acid or both, comprising producing a protein according to claim 13 and contacting a racemic mixture of an α-amino acid amide, an α-hydroxy acid amide or a mixture thereof with the protein produced.

26. A method of preparing an optically active α-amino acid, α-hydroxy acid or both, comprising producing a protein according to claim 17 and contacting a racemic mixture of an α-amino acid amide, an α-hydroxy acid amide or a mixture thereof with the protein produced.

27. A method of preparing an optically active α-amino acid, α-hydroxy acid or both, comprising producing a protein according to claim 18 and contacting a racemic mixture of an α-amino acid amide, an α-hydroxy acid amide or a mixture thereof with the recovered protein.

28. A method of preparing an optically active α-amino acid, α-hydroxy acid or both, comprising producing a protein according to claim 19 and contacting a racemic mixture of an α-amino acid amide, an α-hydroxy acid amide or a mixture thereof with the recovered protein.

29. A method of preparing an optically active α-amino acid, α-hydroxy acid or both, comprising producing a protein according to claim 20 and contacting a racemic mixture of an α-amino acid amide, an α-hydroxy acid amide or a mixture thereof with the recovered protein.

30. A method of preparing an optically active α-amino acid, α-hydroxy acid or both, comprising producing a protein according to claim 21 and contacting a racemic mixture of an α-amino acid amide, an α-hydroxy acid amide or a mixture thereof with the recovered protein.

\* \* \* \* \*